(12) United States Patent
Liu et al.

(10) Patent No.: US 11,541,148 B2
(45) Date of Patent: Jan. 3, 2023

(54) POSS NANOCOMPOSITE HYDROGEL FOR 3D BIOPRINTING

(71) Applicant: THE REGENTS OF THE UNIVERSITY OF MICHIGAN, Ann Arbor, MI (US)

(72) Inventors: Chun Liu, Ann Arbor, MI (US); Kathryn Luker, Ann Arbor, MI (US); Gary Luker, Horsham (GB)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/398,603

(22) Filed: Apr. 30, 2019

(65) Prior Publication Data

US 2019/0328930 A1 Oct. 31, 2019

Related U.S. Application Data

(60) Provisional application No. 62/664,725, filed on Apr. 30, 2018.

(51) Int. Cl.
*A61L 27/20* (2006.01)
*A61L 27/24* (2006.01)
(Continued)

(52) U.S. Cl.
CPC ............ *A61L 27/20* (2013.01); *A61L 27/18* (2013.01); *A61L 27/24* (2013.01); *A61L 27/44* (2013.01);
(Continued)

(58) Field of Classification Search
CPC ...... B33Y 70/00; B33Y 80/00; C09D 189/06; C09D 105/04; A61L 27/56; A61L 27/20; A61L 27/18; A61L 27/24; A61L 27/26; A61L 27/44; A61L 27/52; A61L 27/54; C08L 5/04; C08L 5/00; C08L 89/06
See application file for complete search history.

(56) References Cited

U.S. PATENT DOCUMENTS 7,591,831 B2    9/2009  Parsonage et al.
9,249,254 B2    2/2016  Mather et al.
(Continued)

OTHER PUBLICATIONS

Yang et al. ("Collagen-alginate as bionic for three-dimensional (3D) cell printing based cartilage tissue engineering" in Materials Science & Engineering C 83 (Feb. 1, 2018) 195-201).*
(Continued)

*Primary Examiner* — Blessing M Fubara
(74) *Attorney, Agent, or Firm* — Marshall, Gerstein & Borun LLP

(57) ABSTRACT

Provided is a bioink comprising a mixture comprising a collagen and a polysaccharide, and a polyhedral oligomeric silsesquioxane (POSS), a hydrogel matrix formed from a bioink comprising a mixture comprising a collagen and a polysaccharide, and a polyhedral oligomeric silsesquioxane (POSS), a 3D biomaterial scaffold comprising a hydrogel matrix of the disclosure as a first hydrogel layer and a hydrogel matrix of the disclosure as a second hydrogel layer, optionally having an intervening layer between the first hydrogel layer and the second hydrogel layer, and methods of forming and using same.

38 Claims, 5 Drawing Sheets

(51) Int. Cl.
| | |
|---|---|
| A61L 27/18 | (2006.01) |
| A61L 27/52 | (2006.01) |
| A61L 27/56 | (2006.01) |
| A61L 27/44 | (2006.01) |
| A61L 27/54 | (2006.01) |
| C08L 5/04 | (2006.01) |

(52) U.S. Cl.
CPC .............. *A61L 27/52* (2013.01); *A61L 27/54* (2013.01); *A61L 27/56* (2013.01); *A61L 2300/414* (2013.01); *A61L 2300/416* (2013.01); *C08L 5/04* (2013.01); *C08L 2203/02* (2013.01)

(56) References Cited

U.S. PATENT DOCUMENTS

| | | |
|---|---|---|
| 2015/0094808 A1 | 4/2015 | Macchiarini |
| 2017/0002174 A1 | 1/2017 | Bhagwagar et al. |
| 2017/0172765 A1 | 6/2017 | Solorzano et al. |

OTHER PUBLICATIONS

Ayandele et al. ("Polyhedral Oligomeric Silsesquioxane (POSS)-Containing Polymer Nanocomposites" in Nanomaterials 2012, 2, 445-475).*

Kannan et al. (Polyhedral Oligomeric Silsesquioxane Nanocomposites: The Next Ggeneration Material for Biomedical Applications in Accounts of Chemical Research, 2005, 38, 879-884).*

Chawla et al. ("A polyhedral oligomeric silsesquioxane-based bilayered dermal scaffold seeded with adipose tissue-derived stem cells: in vitro assessment of biomedical properties" in Journal of surgical Research, 188, (2014) 361-372).*

Duan et al. ("Surface Modification and Reinforcement of silica Aerogels using of Polyhedral Oligomeric Silsesquioxane" in Langmuir , Oct. 2012, 15632-15371).*

Ledin et al. ("Branched Polyhedral Oligomeric Silsesquioxane Nanoparticles Prepared via Strain-Promoted 1,3-Dipolar Cycloadditions" Langmuir, 2015, No. 31 (29): 8146-8155).*

Leberfinger et al. ("Concise Review: Bioprinting of Stem Cells for Transplantable Tissue Fabrication" in Tissue Engineering and Regenerative Medicine, 2017, 6:1940-1948).*

3D Bioprinting, Wikipedia entry, downloaded from the Internet at: <https://en.wikipedia.org/wiki/3D_printing> (last updated Jun. 26, 2019).

3D Bioprinters Bring Your Work to Life, Allevi, Philadelphia, PA, downloaded from the Internet at: < <https://allevi3d.com/> (2014).

Bio-ink, Wikipedia entry, downloaded from the Internet at: <https://en.wikipedia.org/wiki/Bio-ink> (last updated Apr. 4, 2019).

BioX Product Brochure on Bioprinting and Bio-ink, Cellink® (2016).

Blaeser et al., 3D bioprinting of cell-laden hydrogels for advanced tissue engineering, Curr. Opin. Biomed. Engineering, 2:58-66 (Jun. 2017).

Cavnar et al., Modeling selective elimination of quiescent cancer cells from bone marrow, Neoplasia, 17(8):625-33 (Aug. 2015).

Cellular BioInk Ready-to-Print Kit (KT-033), RoosterBio® Inc. (publicly available before Apr. 30, 2018).

Crowley et al., Surface modification of a POSS-nanocomposite material to enhance cellular integration of a synthetic bioscaffold, Biomaterials, 83:283-93 (Mar. 2016).

Dababneh et al., Bioprinting Technology: A Current State-of-the-Art Review, J. Manuf. Sci. Eng., 136(6):061016 (Oct. 24, 2014).

Duan et al., Surface modification and reinforcement of silica aerogels using polyhedral oligomeric silsesquioxanes, Langmuir, 28(43):15362-71 (Oct. 2012).

Goole et al., 3D printing in pharmaceutics: A new tool for designing customized drug delivery systems, Int. J. Pharm., 499(1-2):376-94 (Feb. 2016).

Gupta et al., Novel Electrohydrodynamic Printing of Nanocomposite Biopolymer Scaffolds, J. Bioactive and Compatible Polymers, 22(3):265-80 (May 1, 2007).

Kannan et al., Polyhedral Oligomeric Silsesquioxane Nanocomposites:? The Next Generation Material for Biomedical Applications, Acc. Chem. Res., 38(11):879-84 (2005).

Kuo et al., POSS related polymer nanocomposites, Progress in Polymer Sci., 36(12):1649-96 (Dec. 2011).

Lifeink™ Natural Bioinks for 3D Printing, Advanced BioMatrix.

Liu et al., Hybrid collagen alginate hydrogel as a platform for 3D tumor spheroid invasion, Acta Biomaterialia, 75:213-25 (Jul. 2018).

Mironov et al., Nanotechnology in vascular tissue engineering: from nanoscaffolding towards rapid vessel biofabrication, Trends Biotechnol., 26(6):338-44 (Jun. 2008).

Olde Damink et al., Glutaraldehyde as a crosslinking agent for collagen-based biomaterials, J. Materials Sci.: Materials in Medicine, 6(8):460-72 (Aug. 1995).

Sabnis et al., Cytocompatibility studies of an in situ photopolymerized thermoresponsive hydrogel nanoparticle system using human aortic smooth muscle cells, J. Biomed. Mater. Res. A, 91(1):52-9 (Oct. 2009).

Serra et al., Design and fabrication of 3D-printed anatomically shaped lumbar cage for intervertebral disc (IVD) degeneration treatment, Biofabrication, 8(3):0350001 (Jul. 2016).

Silsequioxane, Wikipedia entry, downloaded from the Internet at: <https://en.wikipedia.org/wiki/Silsesquioxane> (last edited May 18, 2019).

Sinha et al., UV-induced DNA damage and repair: a review, Photochem. Photobiol. Sci., 1(4):225-36 (Apr. 2002).

Solouk et al., An Engineering Technique for Improvement of the Patency Rate of Bypass Grafts, Artificial Organs, vol. 37, p. A32 (Jul. 2013).

Spackman et al., 3D printing of fiber-reinforced soft composites: Process study and material characterization, Journal of Manufacturing Processes, 23:296-305 (Aug. 2016).

Stansbury et al., 3D printing with polymers: Challenges among expanding options and opportunities, Dent. Mater., 32(1):54-64 (Jan. 2016).

Stratton et al., Polymeric 3D printed structures for soft-tissue engineering, J. Applied Polymer Sci., 135(24):45569 (Jun. 20, 2018).

Vaezi et al., freeform fabrication of nano-biomaterials using 3D printing, Rapid Prototyping of Biomaterials, pp. 16-74 (2014).

Wang et al., Hydrolytic degradation of POSS-PEG-lactide hybrid hydrogels, Polymer Degradation and Stability, 96(1):123-30 (Jan. 2011).

Yahyaei et al., Synthesis and characterization of polyhedral oligomeric titanized silsesquioxane: A new biocompatible cage like molecule for biomedical application, Mater. Sci. Eng. C Mater. Biol. Appl., 61:293-300 (Apr. 2016).

* cited by examiner

POSS NANOCOMPOSITE HYDROGEL FOR 3D BIOPRINTING

CROSS-REFERENCE TO RELATED APPLICATIONS

This application claims the benefit of U.S. Provisional Application No. 62/664,725, filed Apr. 30, 2018, which application is incorporated herein by reference.

FIELD OF THE DISCLOSURE

The disclosure relates generally to a hydrogel-based bioink for use in 3D bioprinting, hydrogel matrices comprising the bioink, 3D bioprinted scaffolds, and methods of preparing and using same. More particularly, the disclosure relates to a bioink comprising a hydrogel and a polyhedral oligomeric silsesquioxane (POSS) and hydrogel matrices and 3D bioprinted scaffolds comprising same and methods of making and using same.

BACKGROUND

Three dimensional ("3D") bioprinting is a tissue engineering technique that can produce biocompatible complex three dimensional structures from digital models, analogous to conventional 3D printing for plastic based materials. 3D bioprinting is accomplished using materials collectively known as bioinks, which include broad classes of compounds like hydrogels or decellularized extracellular matrix proteins, which can, e.g., create synthetic organ-like structures.

A significant advantage of bioprinting over conventional tissue engineering is the ability to produce multicellular structures that are well organized and, using multiple printer heads, bioligands and signaling molecules can be specifically deposited to direct cellular assembly and architecture, mimicking the dynamics of organioid formation.

The largest current bottleneck in the bioprinting industry is the development of printer compatible bioinks that are affordable, can be loaded with drugs or signaling molecules, and that maintain their designed shape during handling and for a defined time post grafting to the organism. A significant challenge associated with bioinks is associated with the conditions required to cure the gel into a stable structure. There are currently three approaches to cure the printed materials. The first approach is physical crosslinking, which requires specific hydrogen bonding patterns between molecules of the printed material. These networks require strict temperature control during the printing process that is difficult to achieve, resulting in structures with non-uniform composition. The second approach is chemical crosslinking, which provides uniform, rigid structures with excellent mechanical properties. Unfortunately, a large number of crosslinkers are required to produce these structures, which results in materials with poor porosity, preventing the release of embedded drugs or signaling molecules. Additionally, many of the chemicals used to achieve crosslinking are toxic, requiring careful monitoring of the amount of crosslinking agent used to ensure host compatibility. The third approach is UV crosslinking, which provides materials comparable to those achieved with chemical crosslinking strategies, but photoinitiator agents are dose-dependently toxic to cells and prolonged exposure to UV irradiation can cause significant DNA damage that may render embedded cells useless, at best, and malignant, at worst.

Thus, a need exists for bioinks that can be crosslinked in a manner that is compatible with biological materials.

SUMMARY

Provided herein are bioinks comprising a mixture comprising a collagen and a polysaccharide, and a polyhedral oligomeric silsesquioxane (POSS). Also provided are hydrogel matrices formed from bioinks disclosed herein.

Further provided are 3D biomaterial scaffolds comprising a hydrogel matrix of the disclosure as a first hydrogel layer and a hydrogel matrix of the disclosure as a second hydrogel layer, optionally having an intervening layer between the first hydrogel layer and the second hydrogel layer.

Also provided are methods of forming a 3D biomaterial scaffold, comprising printing a first hydrogel layer from the bioink of the disclosure, printing a second hydrogel layer from the bioink of the disclosure on the first layer to form a 3D structure, and optionally curing the 3D structure, thereby forming the 3D biomaterial scaffold.

Still further provided are methods for the sustained release of a drug to a patient in need thereof, comprising grafting a 3D biomaterial scaffold of the disclosure into a surgical site on the patient, wherein the 3D biomaterial scaffold comprises the drug, wherein the drug is either dispersed within the 3D biomaterial scaffold or covalently attached to the POSS.

For the bioink, hydrogel matrix, 3D biomaterial scaffold, and methods of making and using same disclosed herein, optional features, including but not limited to components, conditions, and steps are contemplated to be selected from the various aspects, embodiments, and examples provided herein.

Further aspects and advantages will be apparent to those of ordinary skill in the art from a review of the following detailed description. While the bioink, hydrogel matrix, 3D biomaterial scaffold, and methods of making and using same are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For a more complete understanding of the disclosure, reference should be made to the following detailed description and accompanying drawings wherein.

DETAILED DESCRIPTION

Figure 1A:
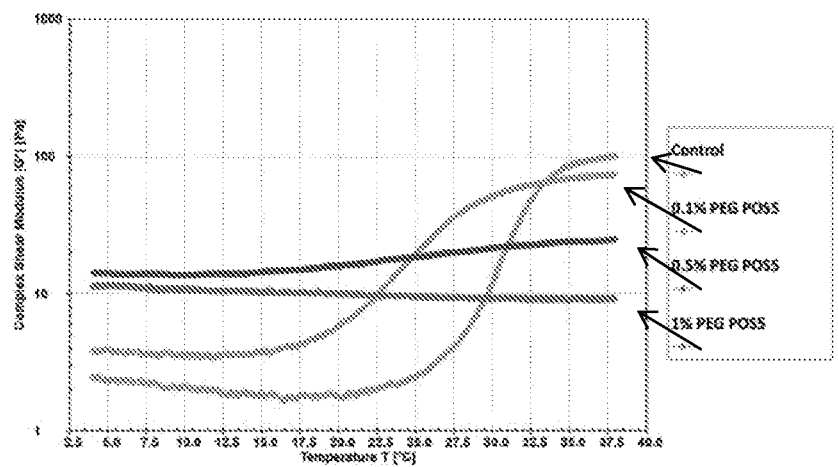
FIG. 1A shows a temperature sweep of 13.3PEG-POSS hydrogel.

Provided herein are hydrogel-based bioink materials compatible with bioprinting which address the current shortfalls within the bioink industry. The bioink comprises a hydrogel material, for example, a mixture of collagen and a polysaccharide, and a polyhedral oligomeric silsesquioxanes (POSS). The incorporation of POSS into a hydrogel-based bioink provides one or more advantages, including, but not limited to, enhancing gelling kinetics and mechanical properties of the hydrogel system, which makes the printing process easier to operate, and/or providing flexibility in grafting other functional groups onto the POSS cage to provide functionalized scaffolds for localized release of drugs, growth factors, or other desired molecules from hydrogel scaffolds.

Bioink

In general, the bioinks disclosed herein comprise a hydrogel mixture and a polyhedral oligomeric silsesquioxane (POSS). The hydrogel mixture can comprise a collagen and a polysaccharide. In some cases, the collagen comprises Collagen Type I. Collagen Type I is found in skin, tendon, vasculature, organs and bone. Collagen, if used alone, has several properties which limit its use in bioprinting applications, including, but not limited to, slow gelation kinetics and poor mechanical stability. These properties can hinder the use of collagen in printing of delicate or precise structures. Advantageously, it was found that the use of a polysaccharide in combination with collagen can provide a hydrogel having enhanced gelling kinetics and improved mechanical stability, relative to collagen alone, thereby providing a stable hydrogel that can be used in bioprinting applications.

In addition to, or as an alternative to, the collagen, the bioink can comprise other thermal-induced gelation materials, for example, methylcellulose. In alternative embodiments, the bioink does not include thermal-induced gelation materials other than collagen. Advantageously, collagen demonstrates heat-up induced gelation, e.g., as the temperature increases from 0 to 37° C., which allows gelation at temperatures at which live cells can survive. In contrast, cool-down induced gelation may require temperatures below 0° C., at which live cells cannot survive.

Without intending to be bound by theory, it is believed that the inclusion of the polysaccharide with the collagen can improve the gelation kinetics and mechanical stability of the resulting hydrogel, relative to collagen alone, due to the simple mechanism of intra- and inter-polymer chain cross-linking of polysaccharides. Without intending to be bound by theory, it is believed that the polysaccharide forms a crosslinked secondary network on top of the collagen network, which increases the rate of gelation of the hydrogel mixture.

The polysaccharide can generally be any polysaccharide that can cross-link to form a stable hydrogel matrix. The mechanism of cross-linking the polysaccharide can be chemical (e.g., covalent interactions) or physical (e.g., ionic interactions). Chemical cross-linking is typically not used for preparing bioprinted materials as chemical cross-linking agents are often toxic compounds that must be removed from the final bioprinted material. Physical crosslinking can include crosslinking by ionic interactions and/or crosslinking by crystallization.

Suitable polysaccharides for use in the bioinks of the disclosure include, but are not limited to, alginate, hyaluronic acid, agarose, heparin, chitosan, gelatin, dextrin, carrageenan, and any combination thereof. In embodiments, the polysaccharide comprises alginate, hyaluronic acid, agarose, heparin, chitosan, gelatin, dextrin, carrageenan or a combination thereof. In some embodiments, the polysaccharide comprises alginate. In some embodiments, the polysaccharide comprises a polysaccharide that is negatively charged at neutral pH, including but not limited to alginate, carrageenan, hyaluronic acid, or a combination thereof. In some embodiments, the polysaccharide comprises a polysaccharide that is positively charged at room temperature, including, but not limited to chitosan. Counterions for forming crosslinks with polysaccharides are well known in the art, for example, alginate and calcium, chitosan and phosphate, and carrageenan and potassium.

Crosslinking of the polysaccharides can be carried out under any suitable conditions. Advantageously, the polysaccharides of the disclosure typically crosslink under mild conditions such as room temperature (about 23° C.) and physiological pH. Alginate is an example of a polysaccharide that can be crosslinked by ionic interactions at room temperature and physiological pH. Therefore alginate-based hydrogels are suitable matrix materials for the encapsulation of living cells and for the release of proteins. Chitosan is an example of an amino-polysaccharide which can be cross-linked with a salt at physiological pH. In the presence of glycerol-phosphate disodium salt, chitosan solution remains liquid below room temperature, but quickly gels when heated The bioink can include the collagen and polysaccharide in any suitable ratio, for example in a ratio of about 50:1 to about 1:50 (w/w, collagen:polysaccharide), about 40:1 to about 1:50, about 30:1 to about 1:50, about 20:1 to about 1:20, about 10:1 to about 1:50, about 5:1 to about 1:50, about 5:1 to about 1:40, about 5:1 to about 1:30, about 5:1 to about 1:20, or about 5:1 to about 1:10. Without intending to be bound by theory, it is believed that as the amount of polysaccharide in the hydrogel mixture increases, the mechanical strength of the resulting hydrogel matrix increases and the hydrogel mixture gels more quickly.

The bioink can further include a solvent. In general, the collagen, polysaccharide, and POSS are soluble in the solvent. Suitable solvents include, but are not limited to, water, ethanol, isopropyl alcohol, and a combination thereof.

The concentration of polysaccharide in the bioink can be in a range of about 1 mg polysaccharide/mL of solvent to about 100 mg/mL solvent, about 1 mg/mL to about 90 mg/mL, about 1 mg/mL to about 80 mg/mL, about 1 mg/mL to about 70 mg/mL, about 1 mg/mL to about 60 mg/mL, about 2 mg/mL to about 100 mg/mL, about 2 mg/mL to about 90 mg/mL, about 2 mg/mL to about 80 mg/mL, about 2 mg/mL to about 70 mg/mL, about 2 mg/mL to about 60 mg/mL, about 2.5 mg/mL to about 100 mg/mL, about 2.5 mg/mL to about 75 mg/mL, or about 2.5 mg/mL to about 60 mg polysaccharide/mL solvent.

The concentration of collagen in the bioink can be in a range of about 0.5 mg collagen/mL solvent to about 50 mg/mL, about 0.5 mg/mL to about 40 mg/mL, about 0.5 mg/mL to about 30 mg/mL, about 0.5 mg/mL to about 20 mg/mL, about 0.5 mg/mL to about 15 mg/mL, about 0.5 mg/mL to about 12 mg/mL, about 1 mg/mL to about 50 mg/mL, about 1 mg/mL to about 40 mg/mL, about 1 mg/mL to about 30 mg/mL, about 1 mg/mL to about 20 mg/mL, about 1 mg/mL to about 15 mg/mL, about 1 mg/mL to about 12 mg/mL, about 1.5 mg/mL to about 50 mg/mL, about 1.5 mg/mL to about 40 mg/mL, about 1.5 mg/mL to about 30 mg/mL, about 1.5 mg/mL to about 20 mg/mL, about 1.5 mg/mL to about 15 mg/mL, or about 1.5 mg/mL to about 12 mg collagen/mL solvent.

POSS

Polyhedral oligomeric silsesquioxanes (POSS) molecules have a cubic-shaped inorganic siloxane ($-Si_8O_{12}$) core with organic functionality at each of the eight corners. POSS can be described by the general formula, $(RSiO_{1.5})_n$, where n is an integer, e.g., 6 to 12, for example, 6, 8, 10, or 12, and each R indicates the organic functionality. POSS-based materials are generally non-toxic and cytocompatible.

POSS molecules are generally soluble and POSS-containing materials can be prepared using two different strategies: (1) based on chemical grafting, where POSS molecules can be chemically linked to a master material at the molecular level by chemical modification of the organic functionality (R groups); or (2) introduced by physical blending. POSS cages are considered to be the smallest possible form of silica, having a size of the POSS cage of about 1.5 nm.

The POSS can be included in the bioink in an amount of about 0.05% to about 25.0%, by weight, based on the total weight of the non-solvent components of the bioink. Without intending to be bound by theory, it is believed that when the POSS is provided in an amount less than 0.05 wt. %, there is negligible change to the gelling kinetics and mechanical stability of the hydrogel matrix formed from the collagen, polysaccharide, and POSS mixture. Further, without intending to be bound by theory, it is believed that as the amount of POSS is increases, e.g., above about 25.0 wt. %, the POSS nanoparticles will aggregate and precipitate out of the bioink. The POSS can be included in the bioink in an amount of about 0.05% to about 25.0%, by weight, based on the total weight of the non-solvent components of the bioink, about 0.05 wt. % to about 20 wt. %, about 0.05 wt. % to about 15 wt. %, about 0.05 wt. % to about 10 wt. %, about 0.05 wt. % to about 5 wt. %, about 0.05 wt. %, to about 1 wt. %, about 0.1 wt. % to about 25 wt. %, about 0.1 wt. % to about 20 wt. %, about 0.1 wt. % to about 15 wt. %, about 0.1 wt. % to about 10 wt. %, about 0.1 wt. % to about 5 wt. %, or about 0.1 wt. % to about 1 wt. %, based on the total weight of the non-solvent components of the bioink.

In embodiments, the POSS comprises a compound having a structure of Formula (I):

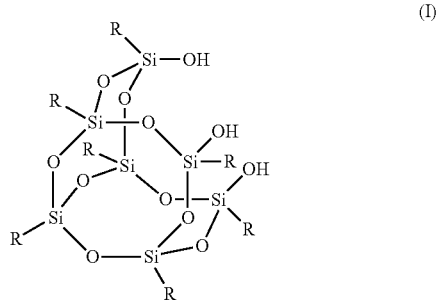

(I)

wherein each R is independently H, $C_1$-$C_{20}$ alkyl, $C_3$-$C_{10}$ cycloalkyl, aryl, $C_1$-$C_{20}$ thiolalkyl, $C_1$-$C_{20}$ aminoalkyl, or $C_1$-$C_{20}$ alkoxyl. In embodiments, each R is independently H, $C_1$-$C_6$ alkyl, or $C_6$ aryl. In embodiments, each R is independently H, methyl, ethyl, n-propyl, isopropyl, n-butyl, t-butyl, isobutyl, or phenyl. In embodiments, at least one R is ethyl, or each R is ethyl. In embodiments, at least one R is isobutyl, or each R is isobutyl. In embodiments, at least one R is phenyl, or each R is phenyl.

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. "Alkoxyl," "thioalkyl," and "aminoalkyl" indicate alkyl groups that have one to three (e.g., 1, 2, or 3, preferably 1) carbon atoms replaced by the indicated heteroatom—O, S, and N, respectively. For aminoalkyl groups, the nitrogen is further substituted with H or a C1-3 alkyl group. The heteroatom can be at the attaching position (i.e., is attached to the Si atom) or at another position in the alkyl chain.

As used herein, the term "cycloalkyl" refers to an aliphatic cyclic hydrocarbon group containing three to ten, e.g., 3 to 8 carbon atoms (e.g., 3, 4, 5, 6, 7, or 8 carbon atoms). The term $O_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

Without intending to be bound by theory, it is believed that the silano groups of the POSS having a structure according to structure (I) crosslink with the hydroxyl groups on collagen molecules during the thermal gelation of collagen.

As demonstrated in the examples, compounds having a structure according to structure (I), wherein each R is isobutyl (TSB POSS), each R is ethyl (TSE POSS), or each R is phenyl (TSP POSS) have been demonstrated to enhance crosslinking in a collagen/polysaccharide hydrogel. Other compounds having a structure according to structure (I) necessarily have three silano groups on the POSS cage, which can facilitate crosslinking in the same was as demonstrated for the TSB POSS, TSE POSS, and TSP POSS.

In embodiments, the POSS comprises a compound having a structure according to Formula (II):

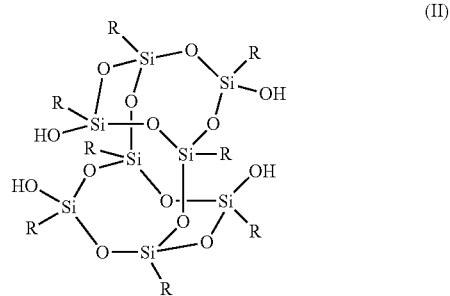

(II)

wherein each R is independently H, $C_1$-$C_{20}$ alkyl, $C_3$-$C_{10}$ cycloalkyl, aryl, or $C_1$-$C_{20}$ alkoxyl, $C_1$-$C_{20}$ thiolalkyl, $C_1$-$C_{20}$ aminoalkyl. In embodiments, each R is independently H, $C_1$-$C_6$ alkyl, or $C_6$ aryl. In embodiments, each R is independently H, methyl, ethyl, n-propyl, isopropyl, n-butyl, t-butyl, isobutyl, or phenyl. In embodiments, each R is ethyl. In embodiments, each R is isobutyl. In embodiments, each R is phenyl.

Without intending to be bound by theory, it is believed that the silano groups of the POSS having a structure according to Formula (II) crosslink with the hydroxyl groups on collagen molecules during the thermal gelation of collagen.

As demonstrated in the examples, compounds having a structure according to Formula (II), wherein each R is phenyl (TetraSP POSS) have been demonstrated to enhance crosslinking in a collagen/polysaccharide hydrogel. Other compounds having a structure according to Formula (II) necessarily have four silano groups on the POSS cage, which can facilitate crosslinking in the same was as demonstrated for the TetraSP POSS.

Without intending to be bound by theory, it is believed that, as the size of the R group increases for POSS of Formula (I) or (II), the R group can sterically block the reaction of the silano groups with the hydroxyl groups of the collagen. Consequently, when R is large (e.g., phenyl), the level of crosslinking is not directly correlated with the amount of POSS included in the bioink. Rather, it is believed that as the concentration of POSS in the bioink increases, the level of crosslinking will achieve a maximum crosslinking, followed by a decrease in the amount of crosslinking due to steric blocking of the silano groups.

In embodiments, the POSS comprises a compound having a structure according to Formula (III):

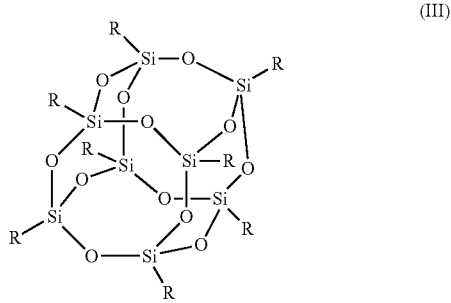

(III)

wherein each R is independently —$(CH_2)_n(OCH_2CH_2)_mOCH_3$ (i.e., a polyethylene glycol (PEG) chain), each n is an integer of 1 to 5 and each m is an integer of 2 to 30. Typically, compounds having a structure according to Formula (III) have a mixture of PEG chains with various chain lengths. In embodiments, R collectively has an average value of m of about 13 or 14.

Without intending to be bound by theory, it is believed that, as the length of the PEG group increases, the preparation of the POSS having a structure according to structure (III) becomes more difficult as the longer chains are more likely to fold and tangle, preventing the end group of the PEG chains from interacting with and attaching to the Si of the POSS. Further, without intending to be bound by theory, it is believed that the PEG functionalities make the POSS highly soluble, allowing it to disperse evenly through the hydrogel during production.

As demonstrated in the examples, compounds having a structure according to Formula (III), wherein R is $CH_2CH_2(OCH_2CH_2)_mOCH_3$, and m has an average value of about 13.3 (denoted 13.3PEG POSS, wherein 13.3 represents the average number of ethylene glycol units) demonstrated reduced temperature requirements and stringency for gelation of the collagen/polysaccharide material. Other compounds having a structure according to Formula (III) have PEG groups on the corners of the POSS cage, which can facilitate reducing the temperature requirements and stringency of gelation in the same was as demonstrated for the 13.3PEG POSS.

The bioink can further include secondary components. In some embodiments, the secondary components are included in the bioink to provide functionality to the resulting hydrogel. Such secondary components are not particularly limited and can include, but are not limited to, drugs, growth factors, signaling groups, fluorescent tags, or a combination thereof. In embodiments, the drug, growth factor, signaling group, fluorescent dye, or combination thereof can be covalently attached to the POSS. For example, one or more of the R groups on the POSS structure can be modified to include the secondary component, or replaced by the secondary component.

In some embodiments, the bioink can include a secondary component and the secondary component can comprise glycosaminoglycan, fibrin, laminin, fibronectin, or a combination thereof. In some embodiments, the bioink can include a secondary component and the secondary component can comprise glycosaminoglycan, fibrin, laminin, or a combination thereof.

When included in the bioink, the total amount secondary component(s) included can be in a range of about 0.1 wt. % to about 10 wt. %, based on the total weight of the bioink. For example, the total amount of secondary component(s) included can be about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1.0 wt. %, about 1.5 wt. %, about 2.0 wt. %, about 2.5 wt. %, about 3.0 wt. %, about 3.5 wt. %, about 4.0 wt. %, about 4.5 wt. %, about 5.0 wt. %, about 5.5 wt. %, about 6.0 wt. %, about 6.5 wt. %, about 7.0 wt. %, about 7.5 wt. %, about 8.0 wt. %, about 8.5 wt. %, about 9.0 wt. %, about 9.5 wt. %, or about 10 wt. %.

In embodiments, the bioink comprises a mixture of collagen and a polysaccharide comprising alginate, and a POSS having a structure according to Formula (I), wherein each R is isobutyl, the collagen is provided in an amount of 3 mg/mL water, the alginate is provided in an amount of 8 mg/mL water, and the POSS is provided in an amount of 0.1 to 1.0% (w/v), based on the total volume of the hydrogel.

In embodiments, the bioink comprises a mixture of collagen and a polysaccharide comprising alginate, and a POSS having a structure according to Formula (III), wherein each R is independently —$(CH_2)_n(OCH_2CH_2)_mOCH_3$, n is 2, the average m is 13.3, the collagen is provided in an amount of 3 mg/mL water, the alginate is provided in an amount of 8 mg/mL water, and the POSS is provided in an amount of 0.1% to 1.0% (w/v), based on the total volume of the hydrogel.

Hydrogel Matrix

A hydrogel matrix is formed upon gelation of the bioink of the disclosure. In embodiments, the POSS is covalently bonded to the polysaccharide of the hydrogel matrix. In embodiments, the POSS is not covalently bonded to the polysaccharide but is dispersed homogeneously throughout the matrix.

The hydrogel matrix is typically porous and the pore size (i.e., diameter) is not particularly limiting. In embodiments wherein live cells are provided in the hydrogel matrix, the pore size can be sufficiently large to allow for nutrient diffusion and cell migration. In embodiments wherein the hydrogel matrix does not include live cells, the pore diameter is not limited. In embodiments, at least 90% of the pores have a diameter in a range of about 5 micron to about 500 micron, for example, about 5 micron to about 400 micron, about 5 micron to about 300 micron, about 5 micron to about 200 micron, about 10 micron to about 500 micron, about 10 micron to about 400 micron, about 10 micron to about 300 micron, or about 10 micron to about 200 micron. In embodiments, at least 50% of the pores have a diameter in a range of about 90 micron to 150 micron, at least 60% of the pores have a diameter in a range of about 90 micron to about 150 micron, at least 70% of the pores have a diameter in a range of about 90 micron to about 150 micron, or about 80% of the pores have a diameter in a range of about 90 micron to about 150 micron.

3D Biomaterial Scaffold

The 3D biomaterial scaffold of the disclosure can include a first hydrogel layer comprising a hydrogel matrix of the disclosure, a second hydrogel layer comprising a hydrogel matrix of the disclosure, and, optionally, an intervening layer between the first hydrogel layer and the second hydrogel layer. In embodiments, the second hydrogel layer is directly adjacent to the first hydrogel layer. In embodiments, the second hydrogel layer is separated from the first hydrogel layer by an intervening layer. The hydrogel material of the hydrogel matrix of the first hydrogel layer can be the same or different from the hydrogel matrix of the second hydrogel layer. In embodiments, the hydrogel matrix of the first layer and the hydrogel matrix of the second layer comprise the same hydrogel material. In embodiments, the hydrogel matrix of the first layer and the hydrogel matrix of the second layer comprise different hydrogel materials.

In embodiments, the 3D biomaterial scaffold can further comprise one or more of live cells and a tissue embedded in the first hydrogel layer, the second hydrogel layer, or both. In embodiments, the 3D biomaterial scaffold can further comprise one or more of live cells and a tissue seeded on the 3D biomaterial scaffold. Suitable live cells for inclusion in the 3D biomaterial scaffold include, but are not limited to stem cells, fibroblasts, epithelial cells, neural cells, and/or cancer cells. Suitable tissues for inclusion in the 3D biomaterial scaffold include, but are not limited to bone, cartilage, skin, muscle, tooth, heart, liver, kidney, blood vessel, and/or trachea.

In embodiments wherein the 3D biomaterial scaffold includes an intervening layer between the first hydrogel layer and the second hydrogel layer, the intervening layer can be a hydrogel layer, a cell-laden layer, or a drug-laden layer, for example. When the intervening layer is a hydrogel layer, the hydrogel layer can having different mechanical and/or biochemical properties than the first hydrogel layer and the second hydrogel layer. In embodiments, a cell-laden layer can be used as the intervening layer to represent a tissue layer. In embodiments, a drug-laden layer can be used as the intervening layer to test drug efficiency and efficacy. Cells and/or drugs provided in the intervening layer can be the same or different as any cells and/or drugs provided in the first hydrogel layer and/or the second hydrogel layer.

Method of Forming 3D Biomaterial Scaffold

The 3D biomaterial scaffold of the disclosure can be formed by printing a first hydrogel layer from a bioink of the disclosure, printing a second hydrogel layer from a bioink of the disclosure on the first layer to form a 3D structure and, optionally, curing the 3D structure, thereby forming the 3D biomaterial scaffold. In embodiments, the second hydrogel layer can be printed directly adjacent to the first hydrogel layer. In embodiments, an intervening layer printed or deposited following printing of the first hydrogel layer and prior to printing the second hydrogel layer.

In general, the 3D biomaterial scaffold is formed using a step-wise or layer-by-layer fabrication technique. In particular, layer formation is performed through repeated deposition followed by gelation/solidification of the bioink. The first hydrogel layer can be formed by depositing the bioink on a stage or substrate, for example, a glass, metal, or polymer substrate, and allowing the bioink to gel. Optionally, the first hydrogel layer can be cured prior to printing the second hydrogel layer. In embodiments, the second hydrogel layer is printed without or before curing the first hydrogel layer. In embodiments, the second hydrogel layer is printed after curing the first hydrogel layer.

The stage is maintained at a temperature in a range of about 0° C. to about 37° C., about 5° C. to about 37° C., about 10° C. to about 37° C., about 15° C. to about 37° C., about 20° C. to about 37° C., 25° C. to about 37° C., about 30° C. to about 37° C., or about 35° C. to about 37° C., to allow the collagen of the liquid bioink to start to gel as it contacts the stage. Gelation can be complete in less than about 1 minute, less than about 45 seconds, less than about 30 seconds, less than about 20 seconds, less than about 15 seconds, less than about 10 seconds, or less than about 5 seconds, for example, within about 2 seconds, within about 3 seconds, within about 4 seconds, within about 5 seconds, within about 10 seconds, within about 15 seconds, within about 30 seconds, or in a range of about 2 seconds to about 1 minute. The amount of time required to gel the bioink to provide the hydrogel layer can depend on the diameter of the printed thread. The first (and subsequent) hydrogel layer must be fully gelled prior to depositing a second (and subsequent) layer on the first hydrogel layer.

In embodiments wherein an intervening layer is added between the first hydrogel layer and the second hydrogel layer, the intervening layer can be a hydrogel layer, a cell laden layer, or a drug laden layer, for example. When the intervening layer is a hydrogel layer, the intervening hydrogel layer can be printed on the first hydrogel layer. Cells and/or drugs provided in the intervening layer can be the same or different as any cells and/or drugs provided in the first hydrogel layer and/or the second hydrogel layer.

In embodiments, the method can further comprise embedding one or more of live cells and tissue into the 3D biomaterial scaffold. In embodiments, the method can further comprise seeding one or more of live cells and tissue onto the 3D biomaterial scaffold. Live cells can be mixed with the bioink solution and printed as part of the bioink. Alternatively, after the 3D biomaterial scaffold is printed, cells or tissue sections can be incorporated into the structure by trapping the cells or tissue sections in the porous of the 3D biomaterial scaffold. Methods of incorporating cells or tissue sections into porous 3D structures are known in the art. Advantageously, because of the heat-up gelation mechanism of collagen, the bioink and resulting hydrogel matrix are maintained at temperatures at which live cells can survive.

Method of Use

The 3D biomaterial scaffold disclosed herein can be grafted into a surgical site on a patient to provide, for example, the sustained release of a drug that is included in the 3D biomaterial scaffold or to promote tissue growth in a patient. A drug, growth factors, or other signaling molecules can be dispersed within the 3D biomaterial scaffold or covalently attached to the POSS molecules of the structure.

The bioink of the disclosure and the 3D biomaterial scaffolds prepared therefrom can be used in a number of technology areas. For example, the technology disclosed herein has application in post-surgical cancer treatments. Chemotherapeutic drugs can be incorporated into the POSS molecules and the 3D structures prepared from the chemotherapy-doped hydrogel can be implanted near sites where tumors are surgically removed, providing a targeted and localized treatment to attack residual tumor cells. Advantageously, such an approach may dramatically reduce the rates of recurrence within cancers associated with solid tumors and/or enhance the efficacy of other adjuvant therapies like radiation treatments. Further advantageously, this approach may be applied broadly to any disease state in which the targeted release of drugs would provide a prognostic benefit.

The disclosed technology can be further be applied as a scaffold for tissue regeneration. The POSS molecules can be functionalized with growth factors or other signaling molecules to promote tissue growth in regions near grafted hydrogels. Specific applications include bone regeneration, nerve regeneration, cartilage regeneration, etc. Advantageously, such an approach may dramatically reduce recovery times associated with major surgeries, provide significant economic benefit stemming from reduced downtime and lower cost medical care given shorter hospital stays, and/or reduce hospital associated risks, such as acquired infections like MRSA or VRSA, due to shorter hospital stays.

The disclosed technology also has application in developing multifunctional in vitro 3D disease models. Given precise control over the spatial and compositional organization of printed tissues, the hydrogel may be used to produce significantly more accurate model systems for studying phenomena like cellular motility and invasion, tissue remodeling, and/or tissue.

The disclosed technology can also be used to produce materials that can be used to coat medical device implants, such as artificial hip joints, to promote bone growth following implantation of the device. Such an approach would remove the need to use materials such as bone cement, which deteriorates over time eventually causing the replacement joint to break free of the socket. At that point, an additional surgical procedure is required to implant a new joint replacement. By filling in the socket with natural bone tissue, issues such as these can ultimately be mitigated, resulting in fewer surgical procedures amongst the elderly population The bioink, hydrogel matrix, and 3D biomaterial scaffold in accordance with the disclosure can be better understood in light of the following examples, which are merely intended to illustrate the bioink, hydrogel matrix, and 3D biomaterial scaffold and are not meant to limit the scope thereof in any way.

EXAMPLES

Preparation of POSS Containing Hydrogels

Collagen Type I was mixed with alginate stock solution (10×DMEM) and cell culture medium (with or without live cells and spheroids) and the solution was adjusted to neutral pH. POSS was then added to achieve a final concentration of 3 mg/ml collagen and 5 mg/ml alginate. The types of POSS tested include 13.3PEG-POSS (i.e., POSS containing a PEG having an average of 13.3 ethylene glycol units, available as PG1190, from Hybrid Plastics, Inc. (Hattiesburg, Miss.), trisilanolisobutyl-POSS (TSB-POSS), trisilanolethyl-POSS (TSE-POSS), trisilanolphenyl-POSS (TSP-POSS), and tetrasilanolphenyl-POSS (TetraSP-POSS). The amount of POSS added into the hydrogels varied between 0.1 and 20% (w/v). After mixing with POSS, the gels were cured in a humidified tissue culture incubator with 5% $CO_2$ for 20 minutes at 37° C. Fresh cell culture medium was then added to the top of the cured gels.

Gelling Kinetics and Mechanical Properties of POSS Enhanced Hydrogel

The prepared hydrogels were then tested for gelling kinetics and mechanical properties. The gelling kinetics of the hydrogel was determined using an MCR 301 Rheometer (Anton Paar USA, Inc., (Ashland, Va.)) (or equivalent) and the compressive modulus of the hydrogel was determined using a MicroSquisher (CellScale (Waterloo, Ontario, Canada)) (or equivalent).

As shown in FIG. 1A, addition of PEG-POSS attenuates the gelation kinetics of collagen, affording a stable gel over a temperature range of 4 to 38° C. Advantageously, the amount of PEG-POSS can be selected to provide a mechanical strength similar to a control collagen/alginate hydrogel crosslinked with 7.5 mM $CaCl_2$ (FIG. 1C). The enhancement in gelling kinetics is a significant improvement for 3D bioprinting with collagen. Gelation of collagen alone by thermo curing requires delicate temperature control during printing processes, and small alterations in temperature either in the printer head or on the stage will highly affect the gel quality. Therefore, the advantageous stability of the hydrogels including PEG-POSS significantly facilitates the 3D bioprinting process without affecting the gel stiffness.

Figure 1B:
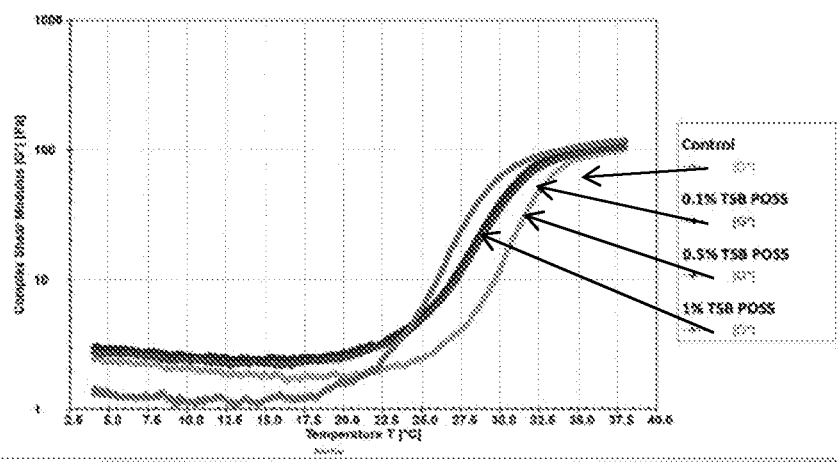
FIG. 1B shows a temperature sweep of TSB-POSS hydrogel.
Figure 1C:
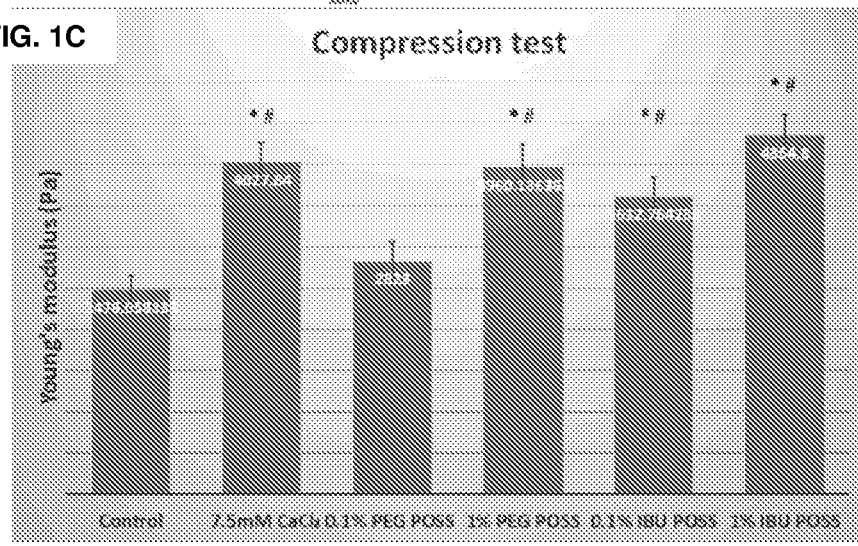
FIG. 1C shows a comparison of the mechanical compressive modulus for each gel type.

FIG. 1B shows the changes of gelling kinetics due to the incorporation of TSB-POSS. In contrast to PEG-POSS, the addition of TSB-POSS improved the gelling of collagen significantly by lowering the gelling temperature and increasing the gelling rate. Without intending to be bound by theory, the advantageous properties are believed to be a result of the chemical reaction between TSB-POSS and collagen, where the active silanol groups on TSB-POSS react with hydroxyl groups on collagen fibers to form a crosslinked network. FIG. 10 shows the addition of TSB-POSS improved the mechanical stiffness of the hydrogels even at 0.1% concentration. One of the drawbacks of using collagen as a bioink is the slow gelation which slows down the entire printing process as the printed hydrogel must be fully cured before a subsequent layer can be provided. By incorporating TSB-POSS, the gelation is accelerated due to chemical crosslinking and the mechanical stiffness is enhanced with adjustable features.

Figure 5:
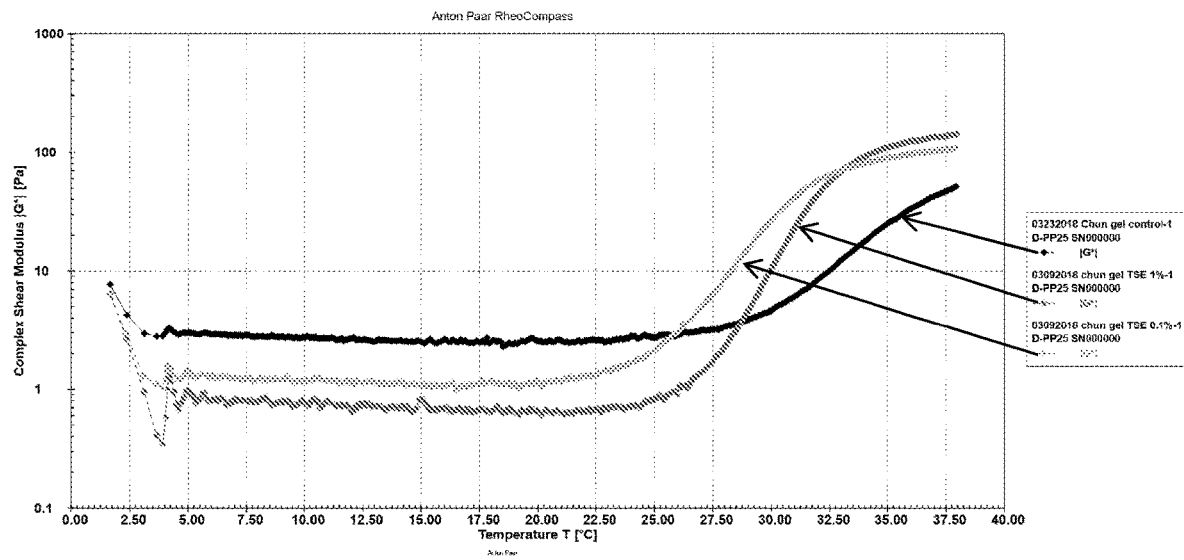
FIG. 5 shows the temperature sweep of TSE-POSS hydrogel.
Figure 6:
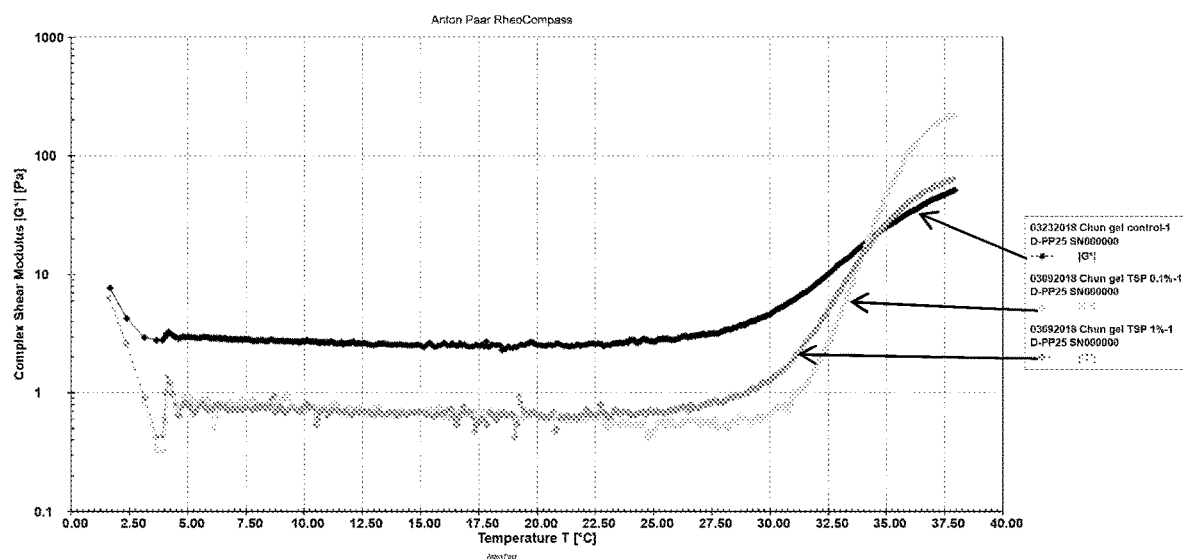
FIG. 6 shows the temperature sweep of TSP-POSS hydrogel.

FIG. 5 shows the temperature sweep of collagen/alginate hydrogels with the addition of TSE-POSS and a control gel having no POSS. TSE-POSS enhanced the crosslinking as indicated by the sharper slopes. FIG. 6 shows the temperature sweep of collagen/alginate hydrogels with the addition of TSP-POSS and a control gel having no POSS. TSP-POSS enhanced the crosslinking as indicated by the sharper slopes. In contrast to the behavior of the TSE-POSS hydrogels, the slope of the TSP-POSS hydrogel having 0.1 wt. % POSS was sharper than the slope of the TSP-POSS hydrogel having 1 wt. % POSS. Without intending to be bound by theory, it is believed that the decrease in the sharpness of the slope for the higher amount of TSP-POSS indicates that the large phenol groups may be hindering the crosslinking reaction. Based on FIG. 1, FIG. 5 and FIG. 6, it is believed that tri-silano POSS acts as a crosslinker during the thermal gelation of collagen.

Figure 7:
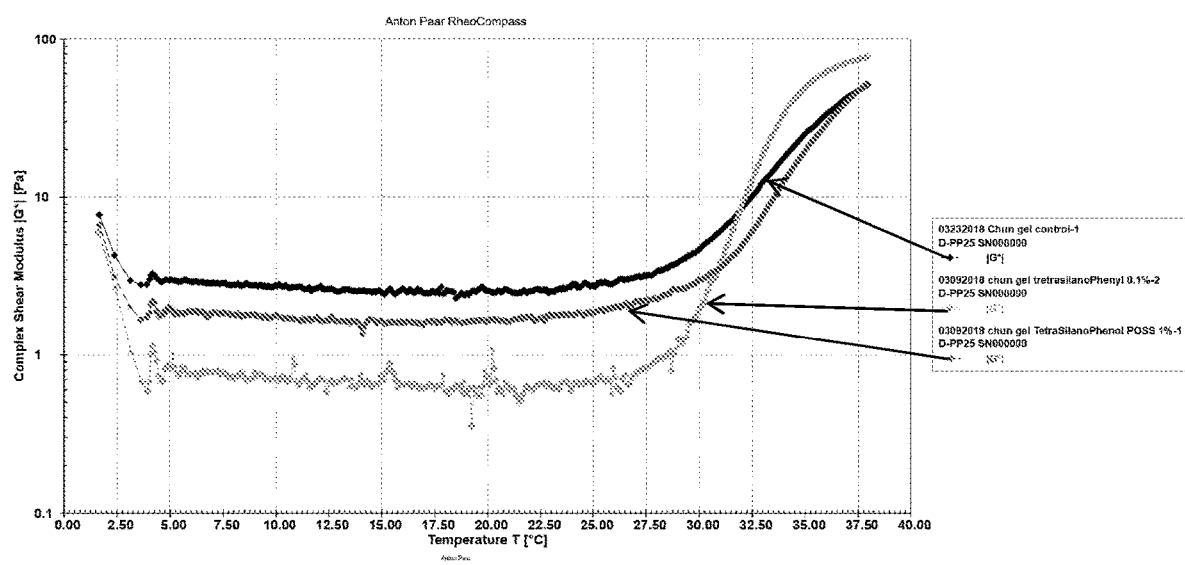
FIG. 7 shows the temperature sweep of TetraSP-POSS hydrogel.

FIG. 7 shows the temperature sweep of collagen/alginate hydrogels with the addition of TetraSP-POSS and a control gel having no POSS. TetraSP-POSS enhanced the crosslinking as indicated by the sharper slopes. Similar to the behavior of the TSP-POSS hydrogels, the slope of the TetraSP-POSS hydrogel having 0.1 wt. % POSS was sharper than the slope of the TetraSP-POSS hydrogel having 1 wt. % POSS. Without intending to be bound by theory, it is believed that the decrease in the sharpness of the slope for the higher amount of TSP-POSS indicates that the large phenol groups may be hindering the crosslinking reaction.

Microstructure and Porosimetry of POSS Enhanced Hydrogel

Figure 2:
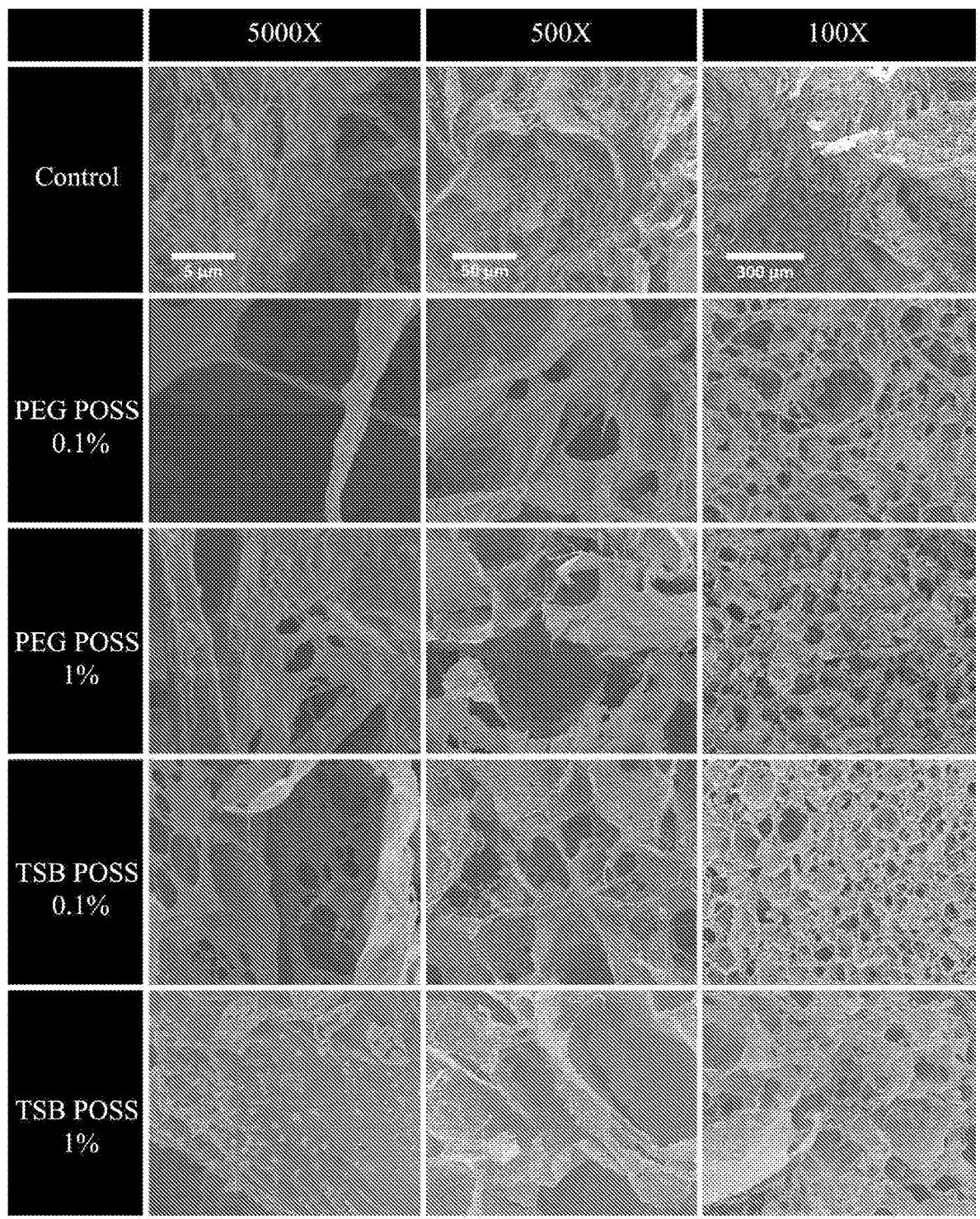
FIG. 2 shows the microstructure of the POSS hydrogels.

The microstructure and porosimetry of the POSS enhanced hydrogels were characterized by Scanning Electron Microscopy (SEM). FIG. 2 shows SEM images of the PEG-POSS hydrogels and the TSB-POSS hydrogels. Compared with the control gel which shows random distribution of collagen fibers with uncrosslinked alginate flakes, the POSS-incorporated gels exhibit uniform microstructures with defined pore geometry and well-distributed pore size. For TSB incorporated gels, the high magnification images clearly show the POSS cages (white triangular particles), indicating a uniform distribution of nanoparticles. The microstructure of hydrogels significantly affects mechanical properties as well as cell growth in the gel, making a uniform gel structure a high priority for bioinks.

Figure 3:
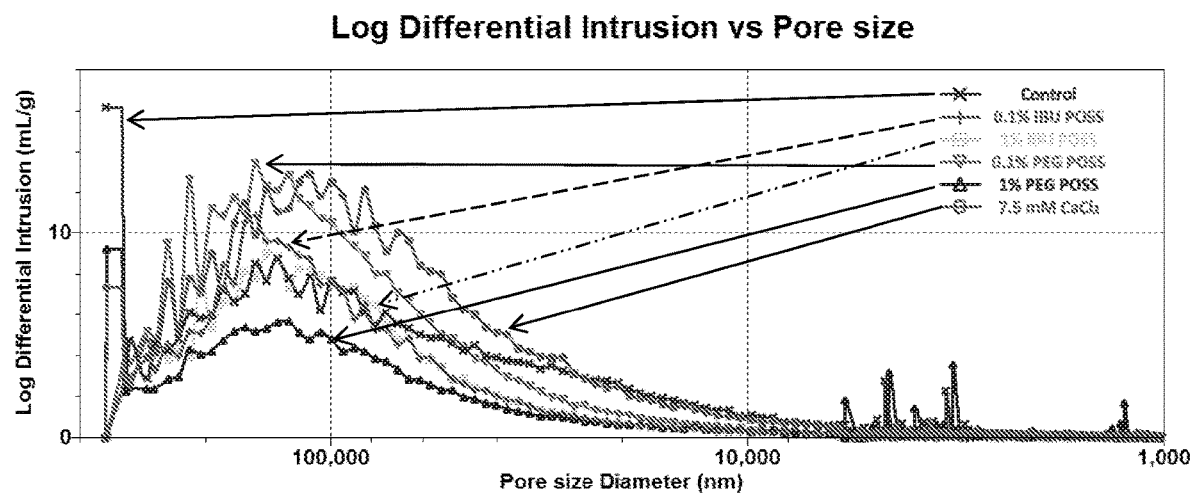
FIG. 3 shows the pore size distribution of POSS hydrogels.

FIG. 3 shows the pore size distribution of the PEG-POSS and TSB-POSS gels. The majority of the pores of the gels have a diameter in a range from 90 to 150 μm. This pore size distribution indicates that the POSS hydrogels have relatively large pores as compared with known bioinks. The large porosity enhances diffusion of nutrients and other exogenous molecules (growth factors or drugs). The large porosity also promotes cell growth in gels and permits cell migration.

Tumor Spheroid Invasion in POSS Enhanced Hydrogel

Figure 4:
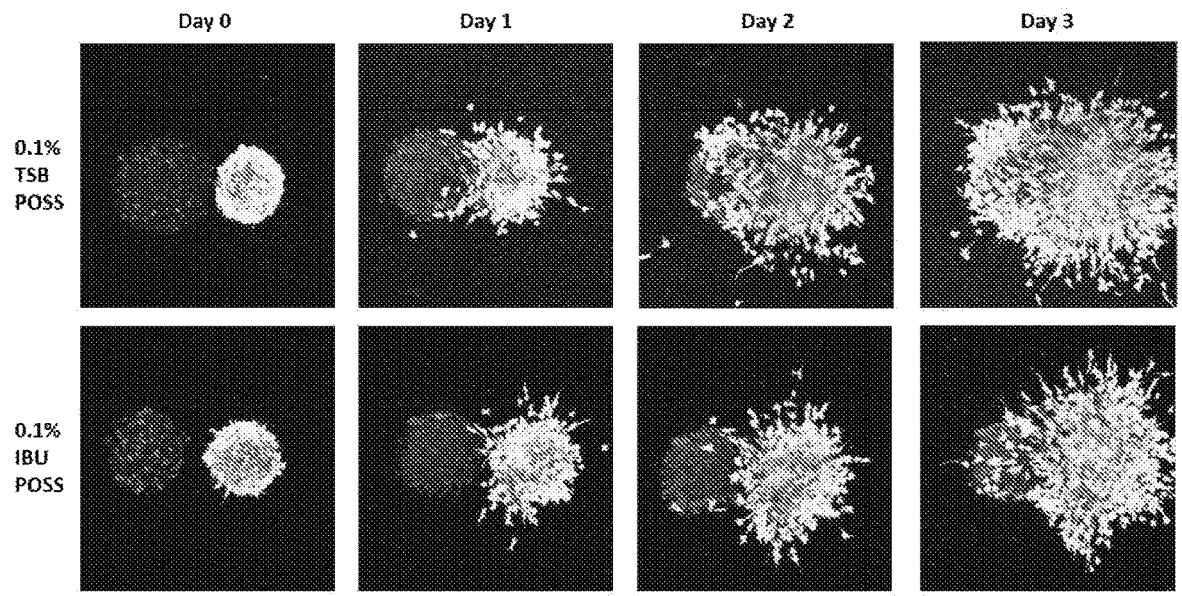
FIG. 4 shows the Invasion of cancer cells from tumor spheroids in PEG-POSS and TSB-POSS incorporated hydrogels.

Cell migration in the PEG-POSS and TSB-POSS hydrogels was modeled using spheroids of human mammary fibroblasts (HMFs) and spheroids of MDA-MB-231 human breast cancer cells. Spheroids were made following known protocol (S. P. Cavnar, A. D. Rickelmann, K. F. Meguiar, A. Xiao, J. Dosch, B. M. Leung, S. Cai Lesher-Perez, S. Chitta, K. E. Luker, S. Takayama, G. D. Luker, Modeling Selective Elimination of Quiescent Cancer Cells from Bone Marrow, Neoplasia 17(8) (2015) 625-633). Once the spheroids formed, the spheroids were embedded into gel solutions and left in an incubator for 30 mins to achieve full gelation. Then 200 μl medium was added on the gel to keep cells alive. A spheroid of HMFs and a spheroid of MDA-MB-231 were placed in the POSS gels and cell migration was imaged for 4 days. Images were taken by 2-photon microscopy using an objective of 25×. HMFs secrete chemoattractant molecules that promote migration of breast cancer cells. FIG. 4 shows migration of cancer cells (right) migrating across the blank gel gap onto the HMF spheroids (left) and eventually wrap the entire HMF spheroid. These results indicate the POSS incorporated hydrogels enable cell growth and migration in a 3D environment.

The foregoing description is given for clearness of understanding only, and no unnecessary limitations should be understood therefrom, as modifications within the scope of the invention may be apparent to those having ordinary skill in the art.

Throughout this specification and claims which follow, unless the context requires otherwise, the word "comprise" and variations such as "comprises" and "comprising" will be understood to imply the inclusion of a stated integer, component, or step or groups of integers, components, or steps but not to the exclusion of any other integer, component, or step or groups of integers, components or steps.

Throughout the specification, where compositions are described as including components or materials, it is contemplated that the composition can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

All patents, publications and references cited herein are hereby fully incorporated by reference. In case of conflict between the present disclosure and incorporated patents, publications and references, the present disclosure should control.

What is claimed:

1. A bioink, comprising:
   an ink mixture comprising:
      a collagen and a polysaccharide;
      a polyhedral oligomeric silsesquioxane (POSS); and
      a solvent for one or more of the collagen, polysaccharide, or POSS;
   wherein the POSS is included in the bioink in an amount of about 0.05% to about 2.0% by weight, based on the total weight of non-solvent components of the bioink;
   wherein when the ink mixture is printed at a temperature in a range of about 0° C. to about 37° C., the ink forms a gel within less than about 1 min.

2. The bioink of claim 1, wherein the polysaccharide comprises alginate, hyaluronic acid, agarose, heparin, or a combination thereof.

3. The bioink of claim 1, wherein the polysaccharide comprises alginate.

4. The bioink of claim 1, wherein the polysaccharide is provided in an amount of 2.5 to 60 mg/mL solvent.

5. The bioink of claim 1, wherein the collagen is provided in an amount of 1.5 to 12 mg/mL solvent.

6. The bioink of claim 1, wherein the collagen and polysaccharide are provided in a ratio (collagen:polysaccharide) of 5:1 to 1:40 (w/w).

7. The bioink of claim 1, wherein the POSS comprises a compound having a structure of Formula (I):

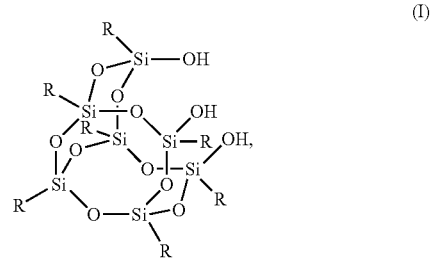

and
   each R is independently H, C1-C20 alkyl, C3-C10 cycloalkyl, aryl, or C1-C20 alkoxyl, C1-C20 thiolalkyl, C1-C20 aminoalkyl.

8. The bioink of claim 7, wherein at least one R comprises isobutyl.

9. The bioink of claim 1, wherein the POSS comprises a compound having a structure of Formula (II):

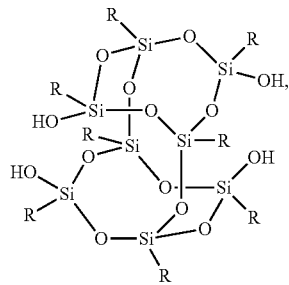

(II)

and each R is independently H, C1-C20 alkyl, C3-C10 cycloalkyl, aryl, or C1-C20 alkoxyl, C1-C20 thiolalkyl, C1-C20 aminoalkyl.

10. The bioink of claim 9, wherein at least one R comprises phenyl.

11. The bioink of claim 9, wherein R, collectively, has an average m of 13 to 14.

12. The bioink of claim 1, wherein the POSS comprises a compound having a structure of Formula (III):

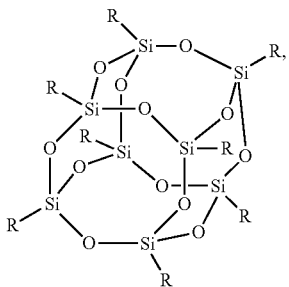

(III)

and each R is independently $-(CH_2)_n(OCH_2CH_2)_mOCH_3$, each n is an integer of 1 to 5 and each m is an integer of 2 to 30.

13. The bioink of claim 1, wherein the polysaccharide comprises alginate, the POSS comprises a compound having a structure of Formula (I):

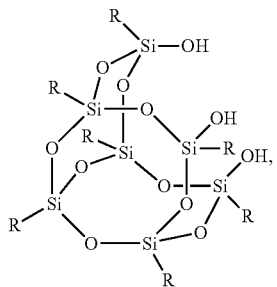

(I)

each R is isobutyl, the bioink further comprises a solvent comprising water, the collagen is provided in an amount of 3 mg/mL solvent, the alginate is provided in an amount of 5 mg/mL solvent, and the POSS is provided in an amount of 0.1% to 1.0% (w/v), based on the total volume of the hydrogel.

14. The bioink of claim 1, wherein the polysaccharide comprises alginate, the POSS comprises a compound having a structure of Formula (I):

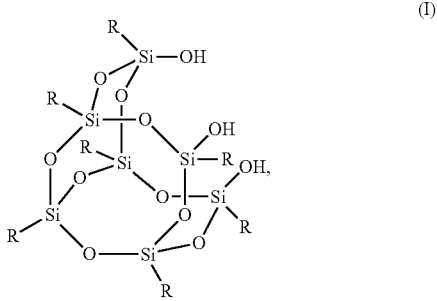

(I)

each R is ethyl, the bioink further comprises a solvent comprising water, the collagen is provided in an amount of 3 mg/mL solvent, the alginate is provided in an amount of 5 mg/mL solvent, and the POSS is provided in an amount of 0.1% to 1.0% (w/v), based on the total volume of the hydrogel.

15. The bioink of claim 1, wherein the polysaccharide comprises alginate, the POSS comprises a compound having a structure of Formula (I):

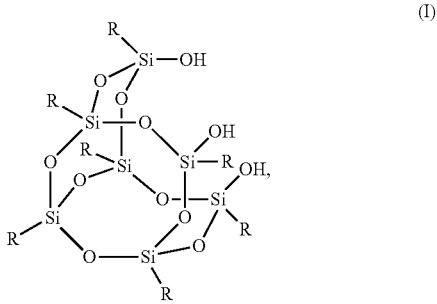

(I)

each R is phenyl, the bioink further comprises a solvent comprising ethanol, the collagen is provided in an amount of 3 mg/mL solvent, the alginate is provided in an amount of 5 mg/mL solvent, and the POSS is provided in an amount of 0.1% to 1.0% (w/v), based on the total volume of the hydrogel.

16. The bioink of claim 1, wherein the polysaccharide comprises alginate, the POSS comprises a compound having a structure of Formula (II):

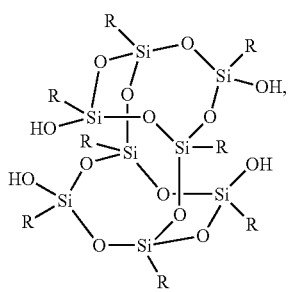

(II)

each R is phenyl, the bioink further comprises a solvent comprising ethanol, the collagen is provided in an amount of 3 mg/mL solvent, the alginate is provided in an amount of 5 mg/mL solvent, and the POSS is provided in an amount of 0.1% to 1.0% (w/v), based on the total volume of the hydrogel.

17. The bioink of claim 1, wherein the polysaccharide comprises alginate, the POSS comprises a compound having a structure of Formula (III):

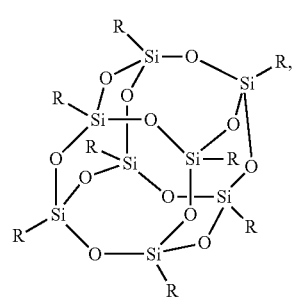

(III)

each R is independently —(CH2)n(OCH2CH2)mOCH3, n is 2, the average m is 13.3, the bioink comprises a solvent comprising ethanol, the collagen is provided in an amount of 3 mg/mL solvent, the alginate is provided in an amount of 5 mg/mL solvent, and the POSS is provided in an amount of 0.1% to 1.0% (w/v), based on the total volume of the hydrogel.

18. The bioink of claim 1, further comprising a drug, growth factor, signaling group, fluorescent tag, or a combination thereof.

19. The bioink of claim 18, wherein the drug, growth factor, signaling group, fluorescent dye, or combination thereof is covalently attached to the POSS.

20. The bioink of claim 1, further comprising one or more of glycosaminoglycans, fibrin, laminin, and a combination thereof.

21. The bioink of claim 20, wherein the one or more of glycosaminoglycans, fibrin, laminin, and a combination thereof is present in the bioink in an amount of 0.1 to 10 wt. %, based upon total weight of the bioink.

22. A hydrogel matrix formed from the bioink of claim 1.

23. The hydrogel matrix of claim 22, wherein the POSS is covalently bonded to the polysaccharide.

24. The hydrogel matrix of claim 22, wherein the POSS is dispersed homogenously throughout the matrix.

25. They hydrogel matrix of claim 22, wherein the hydrogel matrix is porous and has a pore size of 10 micron to 200 micron in diameter.

26. The hydrogel matrix of claim 25, wherein at least 50% of pores are 90 to 150 micron in diameter.

27. A 3D biomaterial scaffold comprising
the hydrogel matrix of claim 22 as a first hydrogel layer and
the hydrogel matrix of claim 22 as a second hydrogel layer,
optionally having an intervening layer between the first hydrogel layer and the second hydrogel layer.

28. The 3D biomaterial scaffold of claim 27, wherein the second hydrogel layer is directly adjacent to the first hydrogel layer.

29. The 3D biomaterial scaffold of claim 27, further comprising one or more of live cells and a tissue embedded in the first hydrogel layer, the second hydrogel layer, or both.

30. The 3D biomaterial scaffold of claim 27, further comprising one or more of live cells and a tissue seeded on the 3D biomaterial scaffold.

31. A method for sustained release of a drug to a patient in need thereof, comprising:
grafting the 3D biomaterial scaffold of claim 27 into a surgical site on the patient, wherein the 3D biomaterial scaffold comprises the drug, either dispersed within the 3D biomaterial scaffold or covalently attached to the POSS.

32. A method of forming a 3D biomaterial scaffold, comprising:
printing a first hydrogel layer from the bioink of claim 1;
printing a second hydrogel layer from the bioink of claim 1 on the first layer to form a 3D structure; and
optionally, curing the 3D structure,
thereby forming the 3D biomaterial scaffold.

33. The method of claim 32, wherein the second hydrogel layer is printed directly adjacent to the first hydrogel layer.

34. The method of claim 32, wherein the second hydrogel layer is printed without or before curing the first hydrogel layer.

35. The method of claim 32, wherein the second hydrogel layer is printed after curing the first hydrogel layer.

36. The method of claim 32, further comprising adding an intervening layer between the first hydrogel layer and the second hydrogel layer.

37. Method of claim 32, further comprising embedding one or more of live cells and tissue into the 3D biomaterial scaffold.

38. The method of claim 32, further comprising seeding one or more of live cells and tissue onto the 3D biomaterial scaffold.

* * * * *